US012797524B2

(12) United States Patent
Stange et al.

(10) Patent No.: US 12,797,524 B2
(45) Date of Patent: Nov. 17, 2026

(54) ARRANGEMENT FOR IMPROVING THE EXCHANGE OF GASES VIA SEMIPERMEABLE MEMBRANES IN AN AQUEOUS MEDIUM

(71) Applicant: ProMedTec Germany GmbH, Rostock (DE)

(72) Inventors: Jan Stange, Rostock (DE); Jan Klaiber, Ganzlin OT Gnevsdorf (DE)

(73) Assignee: ProMedTec Germany GmbH, Rostock (DE)

( * ) Notice: Subject to any disclaimer, the term of this patent is extended or adjusted under 35 U.S.C. 154(b) by 1197 days.

(21) Appl. No.: 17/722,039

(22) Filed: Apr. 15, 2022

(65) Prior Publication Data

US 2022/0339333 A1 Oct. 27, 2022

Related U.S. Application Data

(63) Continuation of application No. PCT/EP2020/078987, filed on Oct. 15, 2020.

(30) Foreign Application Priority Data

Oct. 15, 2019 (DE) ..................... 10 2019 007 144.1

(51) Int. Cl.
*A61M 1/16* (2006.01)

(52) U.S. Cl.
CPC ........ *A61M 1/1621* (2014.02); *A61M 1/1603* (2014.02); *A61M 1/1627* (2014.02); *A61M 1/1654* (2013.01); *A61M 2202/0208* (2013.01); *A61M 2202/0225* (2013.01); *A61M 2202/0413* (2013.01); *A61M 2202/0433* (2013.01)

(58) Field of Classification Search
None
See application file for complete search history.

(56) References Cited

U.S. PATENT DOCUMENTS

| | | | |
|---|---|---|---|
| 3,212,498 A | 10/1965 | McKirdy et al. | |
| 4,001,200 A | 1/1977 | Bonsen et al. | |
| 2006/0019385 A1 | 1/2006 | Smith et al. | |
| 2018/0214055 A1 | 8/2018 | Neudl et al. | |
| 2019/0030232 A1* | 1/2019 | Kreymann .............. | A61M 1/32 |

(Continued)

FOREIGN PATENT DOCUMENTS

| | | |
|---|---|---|
| DE | 26 07 706 A1 | 9/1976 |
| DE | 10 2015 107 269 A1 | 11/2016 |

(Continued)

OTHER PUBLICATIONS

International Search Report of the European Patent Office dated Feb. 9, 2021 for international application PCT/EP2020/078987 on which this application is based.

(Continued)

*Primary Examiner* — Jonathan M Peo
(74) *Attorney, Agent, or Firm* — Walter Ottesen, P.A.

(57) ABSTRACT

Provided are methods and arrangements wherein gases are removed via semipermeable membranes from aqueous, optionally complex biological substance mixtures, by dialysis in an aqueous medium. Special carrier molecules for gases are included in the dialysate that are regenerated in the dialysate circuit so that they can be used for further gas exchange cycles on the membrane.

20 Claims, 6 Drawing Sheets

(56) References Cited

U.S. PATENT DOCUMENTS

| | | | |
|---|---|---|---|
| 2020/0069859 | A1 | 3/2020 | Klewinghaus |
| 2020/0069860 | A1 | 3/2020 | Rammo et al. |
| 2021/0162109 | A1 | 6/2021 | Neudl et al. |

FOREIGN PATENT DOCUMENTS

| | | | | |
|---|---|---|---|---|
| DE | 10 2017 216 689 | A1 | 6/2018 | |
| WO | WO-9817333 | A2 * | 4/1998 | .......... A61M 1/1696 |
| WO | 2017/064285 | A1 | 4/2017 | |

OTHER PUBLICATIONS

Translation and Written Opinion of the International Searching Authority dated Feb. 9, 2021 for international application PCT/EP2020/078987 on which this application is based.

* cited by examiner

ARRANGEMENT FOR IMPROVING THE EXCHANGE OF GASES VIA SEMIPERMEABLE MEMBRANES IN AN AQUEOUS MEDIUM

CROSS REFERENCE TO RELATED APPLICATIONS

This application is a continuation application of international patent application PCT/EP2020/078987, International Patent Publication No. WO2021074267A1, filed Oct. 15, 2020 designating the United States and claiming priority from German application 10 2019 007 144.1, German Patent Application Publication No. DE102019007144A1, filed Oct. 15, 2019, and the entire content of both applications is incorporated herein by reference.

TECHNICAL FIELD

The present disclosure relates to methods and arrangements for improving the exchange of gases across semipermeable membranes in an aqueous environment.

BACKGROUND

The input of oxygen and the removal of carbon dioxide from complex and/or biological fluids is, for example, used in the treatment of blood.

In this case, the prior art is based on so-called oxygenators, which consist of semipermeable membranes composed of hydrophobic porous material. In general, the pores of oxygenators are impermeable to blood cells. The blood is guided along one side and the gas, for example air, oxygen or other gas mixtures, is guided along the other side. Gas exchange initially takes place at the interface between serum and gas phase, where the gases are initially present in a physically dissolved state in the serum and are in communication with red blood cells.

Initially, the hydrophobicity of the material prevents the permeation by the serum from the blood side, but hydrophilization occurs over time, for example owing to deposition of amphiphilic proteins on the surface and the inner surface of the membrane in the case of blood. This increases the distance which must be covered by gases physically dissolved in the liquid phase. In the case of the hollow-fiber membranes that are usually used, the blood is therefore also not guided on the inside of the hollow fiber, as in the case of dialysis with commercially available artificial kidneys, but on the outside, since the pressure drop over the oxygenator on the blood side is thereby lower owing to the higher cross-section for flow. Compared to hemodialysis, this also leads to more turbulences in the blood, which for their part speed up coagulation processes.

The lack of hemocompatibility of existing extracorporeal membrane oxygenation (ECMO) membranes and the need for anticoagulation still lead to serious and potentially life-threatening complications.

This method is currently the most commonly used method for oxygenation and CO2 removal. In the case of the required input of oxygen, high blood flows (up to 5 l/min) are often necessary for sufficient effectiveness; however, if oxygenation via the lungs should be sufficient, but the exhalation of CO2 too low, CO2 can also be effectively removed at slower blood flows. This makes the use of extracorporeal circuits for dialysis therapy, which are generally below 500 ml/min, attractive for parallel CO2 removal.

Between 10-30% of ventilated patients are also dialyzed at the same time, since the most common complication in intensive care units is secondary kidney failure with lung failure as a consequence of infections and sepsis.

Since ventilation involves the need to build up nonphysiological positive pressure in the lungs in order not only to bring O2 into the blood via ventilation but also to be able to remove CO2 effectively, what can occur relatively rapidly is ventilation-induced alveolar damage, which delays withdrawal and prolongs recovery. This increases the number of bed days under ventilation, which are expensive, and also the morbidity rate and even the mortality rate. In the past, it was found that CO2 removal is possible by the classic artificial lung even at relatively low blood flows, as are used in continuous dialysis. With this method, the blood is successively conducted over a dialyzer and an oxygenator, which removes CO2. This technique is expensive and increases blood contact with polymer plastic surfaces. The technique is advertised and used by the market leader Baxter under the brand name PrismaLung international.

The idea of simultaneously using the dialyzer for CO2 removal was first proposed by the company HEPAWASH. However, the technology from HEPAWASH involves increasing the pH in the dialysate, which increases CO2 solubility and can counterbalance respiratory acidosis in the blood. In addition, there is a limit to the room for maneuver, since there is the risk of alkalosis due to sodium hydroxide. The method has so far not proven effective in controlled clinical studies as means for CO2 removal.

In the case of CO2 removal parallel to dialysis, another problem is that dialysis generally commonly involves using sodium bicarbonate as dialysate buffer in order to counterbalance the metabolic acidosis of kidney failure. In this case, sodium bicarbonate is in equilibrium in solution with CO2 and sodium hydroxide, which increases the CO2 load. In addition, continuous dialysis involves increasing use of Na citrate as a regional anticoagulant, the metabolism of which can form even more sodium bicarbonate.

DE 102017216689 A1 discloses a dialyzer and a blood treatment element for a further extracorporeal blood therapy, for example a gas exchanger which is arranged in series in a common extracorporeal blood circuit for this purpose.

DE 2607706 C3 discloses a water-soluble, polymerized cross-linked hemoglobin, a method for preparation thereof and use thereof.

US 2019/0030232 A1 is based in general on a method suitable for extracorporeal lung support. The method comprises contacting blood with a dialysis fluid separated by a semipermeable membrane. Prior to contacting of blood and dialysis fluid, oxygen is introduced into the blood and/or into the dialysis fluid, so that it reaches the dialysate side of the dialyzer in a physically dissolved state in the dialysate. CO2 and O2 are exchanged across the membrane only through physical dissolution in the aqueous solution. US 2019/0030232 A1 takes advantage of the Haldane effect in the extracorporeal contacting step.

US 2006/0019385 A1 discloses an apparatus and a method for growing cells up to a high density, products therefrom and use thereof. In certain advantageous embodiments, further oxygenation means are included. Alternatively or additionally, the oxygenation means can comprise the introduction of oxygen and/or an oxygen source or oxygen carrier into the cell culture, either alone or in combination with one or more other gases and/or gas sources or gas carriers.

U.S. Pat. No. 3,212,498 A describes a cell culture apparatus in which the cells are separately oxygenated and dialyzed by two separate membranes.

DE 102015107269 A1 discloses a dialyzer having a blood circuit that, with a simple and compact structure, is suitable for removal of both hydrophilic and hydrophobic substances from the blood. The dialyzer contains a double pump unit which has a single drive and the first pump unit of which is the dialysate pump, having one or more sensors for detection of toxins contained in the dialysate of the dialysate circuit, having a display unit for display of the operating data of the dialyzer and/or the data of the toxins contained in the dialysate of the dialysate circuit as gathered by the sensors. The dialysate is an albumin which can remove both hydrophilic and hydrophobic substances from the blood.

SUMMARY

Provided are methods of removing gases such as CO2 or oxygen across semipermeable membranes in an aqueous environment on both sides in a simplified manner and at a relatively high rate.

The discoveries described herein are based on the surprising observation that oxygen can be delivered even from an aqueous dialysate into the blood via a commercially available dialyzer in a highly effective manner across the semipermeable membrane, if there is present on the dialysate side a soluble oxygen carrier that can carry the oxygen in an aqueous dialysate as closely as possible to the blood side. Even in the case of hydrophilic dialysis membranes, it was possible to observe that, surprisingly, the gas, which is actually hydrophobic, is delivered to the blood at a high rate, even if the dialysis membrane is practically impermeable to dissolved hemoglobin. Hemoglobin present in the inner porous structure speeds up this transfer.

What is special about the methods described herein is that the composition or solution to be influenced contains corpuscular (>1 um in size) gas carriers, for example erythrocytes, and that the gas carrier used in the dialysate is a molecular gas carrier (for example, hemoglobin or related proteins) which itself does not pass through the membrane.

The oxygen arrives rapidly on the blood side, where it gets into the erythrocytes, thereby actively displacing at a high rate the CO2 incorporated in the hemoglobin of the erythrocytes and forcing the CO2 into the aqueous phase of the blood, from where it, by reacting with water, becomes carbonic acid, which is in turn converted into hydrogen ions and bicarbonate ions. These reactions can be additionally promoted by carbonic anhydrase. In any case, carbonic acid ions as well as bicarbonate ions and hydrogen ions can be easily removed by dialysis into the dialysate. If the oxygen carriers in the dialysate are hemoglobin itself, the transfer effect is increased, since the CO2 is now picked up on the dialysate side by the hemoglobin, where it speeds up the removal of the oxygen from the dialysate hemoglobin by "displacement." O2 and CO2 can thus be exchanged very easily across the dialysis membranes in an aqueous environment. The loading/unloading of the dialysate hemoglobin with respect to oxygen and CO2 can then take place in a secondary manner by various processes, for example by electrolysis or photosynthesis, which would not be easily possible in complex biological fluids such as in blood. In any case, the use of a classic oxygenator in the hemoglobin dialysate is possible, and a more effective exchange than in the case of blood oxygenation is also possible here, since the much smaller hemoglobin (between 10 and 20 nm in size) can get closer to the gas phase in the oxygenator than an erythrocyte (approx. 7 μm in size and ellipsoidal). In addition, on the dialysate side, the concentration of the hemoglobin can be set higher than the concentration of the blood hemoglobin, thereby providing an additional increase in the mass transfer of CO2 and oxygen. The procedures described herein are naturally not limited to the exchange of O2 for CO2 and vice versa and to hemoglobin. A similar membrane-crossing effect from one transport molecule to another would be expected in the case of removal of carbon monoxide, which should for example be removable by highly concentrated hemoglobin. It would also be possible for oxygen to be transported and exchanged via related proteins, for example leghemoglobin. To function, what is required is a thin partition layer between blood and dialysate protein (for example, a few nanometers in some cases for asymmetric dialysis membranes, and in this case, the closer the proximity, the smaller the carrier protein in the dialysate, though there should not be any substantial penetration through the membrane) and also reversible binding of the gas by the carrier protein or the various carrier proteins. In addition, in other embodiments, gas is introduced into biological or complex chemical fluids and gas is removed from biological or complex chemical fluids.

Also disclosed are methods of influencing the concentration of gases such as oxygen (O2) and/or carbon dioxide (CO2) in a composition or a solution, where the composition or the solution is guided one-sidedly along an asymmetric, semipermeable membrane. In such embodiments, a dialysate is guided in a closed circuit on the other side of the same membrane, wherein the dialysate contains a gas carrier for at least one of the gases to be influenced. Optionally, in such embodiments, the closed circuit contains an oxygenator.

In some embodiments, the composition or solution to be influenced contains corpuscular gas carriers, for example erythrocytes, and the gas carrier for at least one of the gases to be influenced is molecular hemoglobin or some other related protein.

In various embodiments, the gas carrier gets close to the composition or the solution owing to an asymmetric pore structure of the membrane with more-open pores on the dialysate side of up to below 50 μm, or below 1 μm, or below 100 nm, wherein the gas carrier, however, passes through the membrane to an extent of not more than 10%, or less than 0.1%, or less than 0.01%. Thus, oxygen (O2) diffuses into the composition or the solution over a shortest possible distance and, at the same time, carbon dioxide (CO2) is withdrawn from the composition or the solution into the dialysate by diffusion over a shortest possible distance without the gas carrier itself passing through the membrane.

In certain embodiments, the loaded or unloaded gas carrier is regenerated in a closed recirculation circuit in a secondary manner via a device by loading and/or unloading of gas. The regeneration of the gas carrier in the dialysate is accomplished by the oxygenator, which regenerates the carrier-bearing dialysate by withdrawal of carbon dioxide (CO2) and/or fresh new input of oxygen (O2).

In the case of one embodiment, the membrane employed in such methods is an asymmetric high-flux dialysis membrane having a cut-off between 120 and 1 kDa, or between 60 and 10 kDa, or between 20 and 50 kDa.

In one embodiment, the dialysate comprises molecular hemoglobin having a molecular weight of less than 1 megadalton (approx. 20 hemoglobin tetramers, cross-linked), or less than 500 kDa (approx. 10 hemoglobin tetramers, cross-linked), or below 60 kDa (one tetramer).

In the case of one embodiment of the method, the dialysate is employed in the extracorporeal treatment of blood, which comprises electrolytes, buffer, sugar, molecular monomeric or multimeric hemoglobin, and/or albumin as components. In this case, the albumin is included as a stabilizer for the hemoglobin and as a buffer for ions. The electrolytes, buffer, and glucose vary within the concentrations of commercially available concentrates, wherein the molecular hemoglobin is concentrated in the concentration between greater than 0 g/l up to the technical solubility limit, or above 30 g/l, or above 70 g/l, and albumin has a concentration of between greater than 0 g/l up to the technical solubility limit, or above 50 g/l, or above 200 g/l.

In the case of a further embodiment, the dialysate comprises carbonic anhydrase present as a monomer or functionally cross-linked as a dimer or multimer in order to allow passage into the open-pore dialysate side of the membrane, and to prevent passage into the composition or solution to be influenced on the narrow-pore side of the membrane to an extent of at least 80%, 95%, or above 99%.

In such embodiments, the membrane is simultaneously used for detoxification by dialysis or filtration in the context of blood purification methods in dialysis or apheresis methods.

The arrangement for influencing the concentration of gases such as oxygen (O2) and/or carbon dioxide (CO2) in a composition or a solution comprises two circuits, wherein a first circuit supplies the composition or the solution one-sidedly along a narrow pore side of an asymmetric, semipermeable membrane, from a pool via hoses and pumps. The composition or the solution is then conducted back into the pool via hoses. A second circuit supplies a dialysate on the other side, along an open-pore side of the asymmetric, semipermeable membrane, via hoses and pumps. The dialysate comprises a gas carrier in the form of molecular hemoglobin or other related proteins for at least one of the gases to be influenced and is then conducted back via hoses into a recirculation circuit over a device for regeneration by loading and/or unloading of gases.

In various embodiments described herein, the pumps are roller pumps, impeller pumps, or membrane pumps, and the asymmetric, semipermeable membrane is in some embodiments a flat or hollow-fiber membrane.

The device for regeneration is in some embodiments a commercially available oxygenator.

In some embodiments, the dialysate in the closed circuit is enriched with gas carriers such as molecular hemoglobin, wherein the dialysate is regenerated in the device for regeneration by fresh new input of oxygen (O2) and/or by withdrawal of carbon dioxide (CO2).

In certain embodiments, the composition or the solution is blood or plasma. Such embodiments also optionally include a dialyzer which allows diffusive transfer of pore-crossing molecules from the blood or plasma into a dialysate through a semipermeable membrane.

In the case of one embodiment, for extracorporeal treatment of blood or plasma in a closed circuit, the dialysate is regenerated both by switching on the device for regeneration and by additional adsorption and/or dialysis and/or filtration for material removal or input.

The device for regeneration comprises in some embodiments assimilative biological systems that convert carbon dioxide and water into glucose and oxygen on the basis of photosynthesis under the influence of light, for example isolated chloroplasts.

In the case of a further embodiment, the device for regeneration comprises electrochemical processes for oxygen production, for example electrolysis.

CO2 is eliminated by physicochemical reactions, for example dialysis against alkaline dialysates or precipitation in calcium hydroxide.

The methods and the apparatuses described herein are used in some embodiments outside of therapies, for example for life support for high-density cell cultures (for example, ELAD cartridges) or for isolated or interconnected organs, for example for research, donation or production purposes. These are generally supported by blood or by biological fluids similar to blood that frequently have to be dialyzed or oxygenated, or both, in a secondary manner. The goal of such methods is performing the regeneration of dialysate in a laboratory. The pool in such embodiments is a bioreactor or organ(s).

Advantages of the methods and arrangements described herein, especially in the case of introducing gas into and removing gas from biological fluids, especially blood, include the absence of a liquid/gas phase interface during gas exchange, which has advantages with respect to biocompatibility/hemocompatibility. Proteins can denature upon contact with air or gases, for example coagulation and complement activation occur particularly in blood.

With this method, the hollow-fiber systems do not need to be perfused on the outside for gas exchange with blood (this is the prior art in many cases, where turbulences with additional coagulation and complement activation occur); blood perfusion within hollow-fiber systems allow better rheology and less coagulation induction.

One major advantage of the methods described herein is that multiple processes are possible at the same time (detoxification of water-soluble and/or lipophilic toxins, for example, by additional albumin dialysis, can be carried out across the same membrane as the "gas exchange"; in addition, nutrients can be input from the dialysate side and electrolytes and the pH can be balanced). As a result, exposure to the biomaterial surface is reduced, and there is less stress for the biological fluid or blood.

Since oxygenation and CO2 depletion of hemoglobin (Hb) may be achieved exogenously (indirectly) in an inert protein mixture (Hb/alb/dialysate), alternative gas-exchange technologies are possible, such as electrolysis, CO2 precipitation in calcium hydroxide, or dialysis against alkaline dialysates or assimilative organelles (for example, chloroplasts). The described methods can be performed even under extreme conditions where possibly no gases, but electricity or light, can be used, for example in space.

BRIEF DESCRIPTION OF THE DRAWINGS

The methods and arrangements provided herein will now be described with reference to the drawings wherein.

DESCRIPTION OF THE PREFERRED EMBODIMENTS

Example 1

Figure 1:
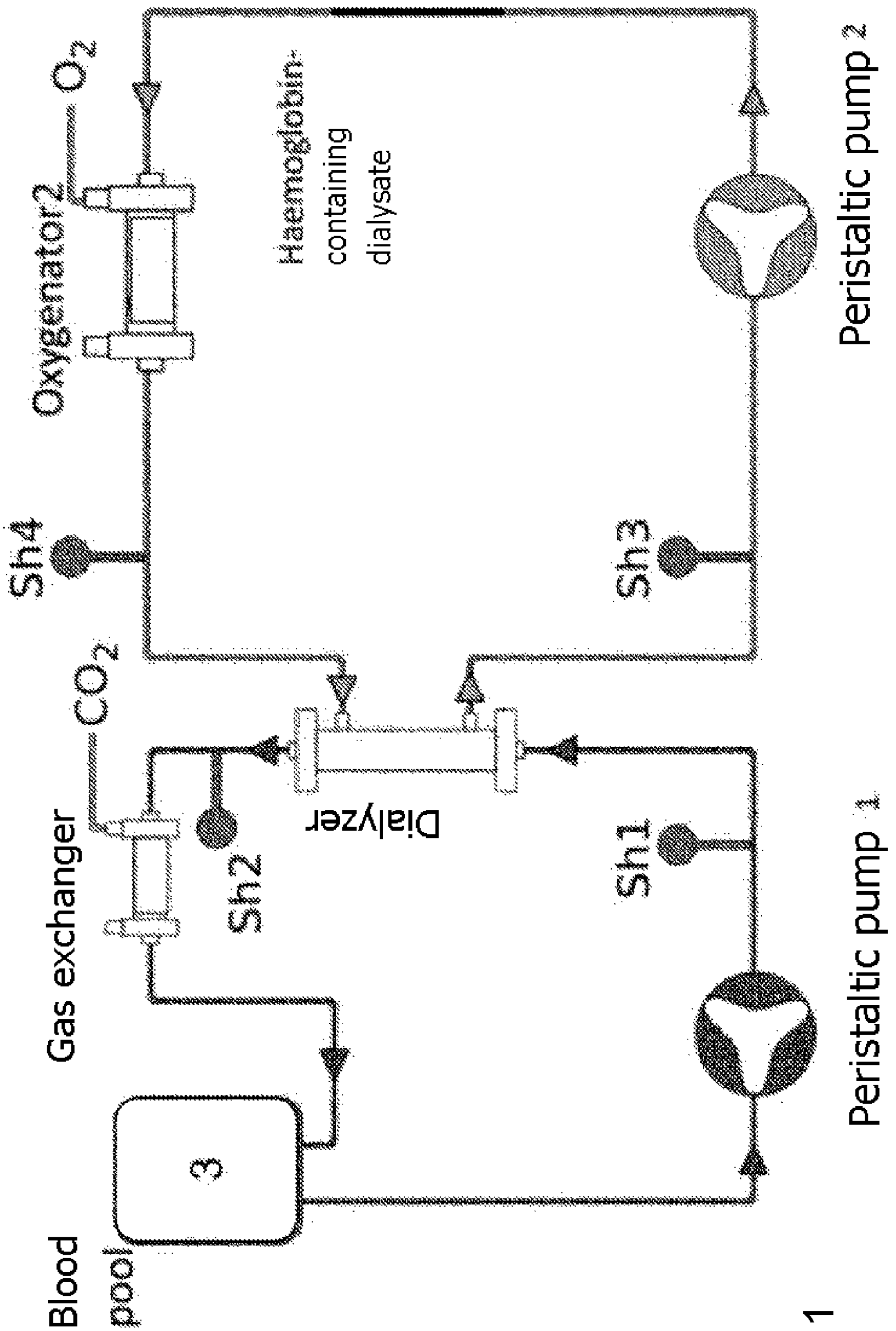
FIG. 1 shows the structure of a closed circuit, wherein the circuit comprises an oxygenator for input of oxygen and for removal of CO2.

$CO_2$-enriched blood is pumped at a rate of 200 ml/min through the hollow fibers of a dialyzer (ideally having an asymmetric membrane, for example polysulfone in a Fresenius FX1000 CORDIAX™), along the dialysate side of which a dialysis fluid containing approx. 30 g/l hemoglobin is conducted, which dialysis fluid likewise recirculates at 200 ml/min in a closed circuit, the circuit containing an oxygenator for input of oxygen and for removal of $CO_2$. The structure is depicted in FIG. 1. Initially, the oxygenator is without an influx of oxygen. Despite a circling solution of hemoglobin dialysate, $CO_2$ clearance decreases over time, since the dialysate hemoglobin is enriched with $CO_2$. After 2.5 minutes, the supply of $O_2$ to the oxygenator is adjusted to 600 ml/min. The effect on $CO_2$ clearance is depicted in FIG. 2.

FIG. 1 shows a blood circuit (hematocrit approx. 40%) which is driven by a peristaltic pump 1 and flows through a dialyzer on the inside of the hollow fibers. The dialyzer is a commercially available asymmetric polysulfone high-flux dialyzer (sieving coefficient for albumin <10%, or <1%), though alternative materials can also be used, such as polyamide, polyethersulfone, et cetera. The membrane need not be a hollow-fiber membrane but in some instances is a flat membrane. Upstream and downstream of the dialyzer, the blood gases are measured at the sampling points SH1 and SH2. In order to simulate endogenous $CO_2$ poisoning, $CO_2$ is "blown in" downstream of the sensor SH2 and immediately upstream of the pool 3 for a composition or a solution, blood in the embodiment, via a gas exchanger (for example, oxygenator). The dialysate is a hemoglobin solution which comprises approx. 30 g/l hemoglobin and which is likewise driven by a pump 2, for example a peristaltic pump. In an alternative embodiment, optionally carbonic anhydrase can be used in the dialysate, which in some instances increases the effect. Owing to the asymmetric membrane, the molecules of the hemoglobin solution penetrate into the membrane structure from the dialysate side in order to get relatively close to the erythrocytes of the blood. On the dialysate side as well, blood gas analysis is performed upstream of SH4 and downstream of SH3. At the same time, $O_2$ is blown in and exchanged for $CO_2$, similar to a simple oxygenator, upstream of the sensor SH4 in the direction of flow. The dialysate can be operated in cocurrent or countercurrent, preference being given to countercurrent. The effect of "oxy-carbo-dialysis" with $O_2$-enriched and $CO_2$-depleted hemoglobin dialysate on the $CO_2$ clearance of the dialyzer is demonstrated in FIG. 2. The effect on the oxygen saturation of the blood is shown in FIG. 3.

Figure 2:
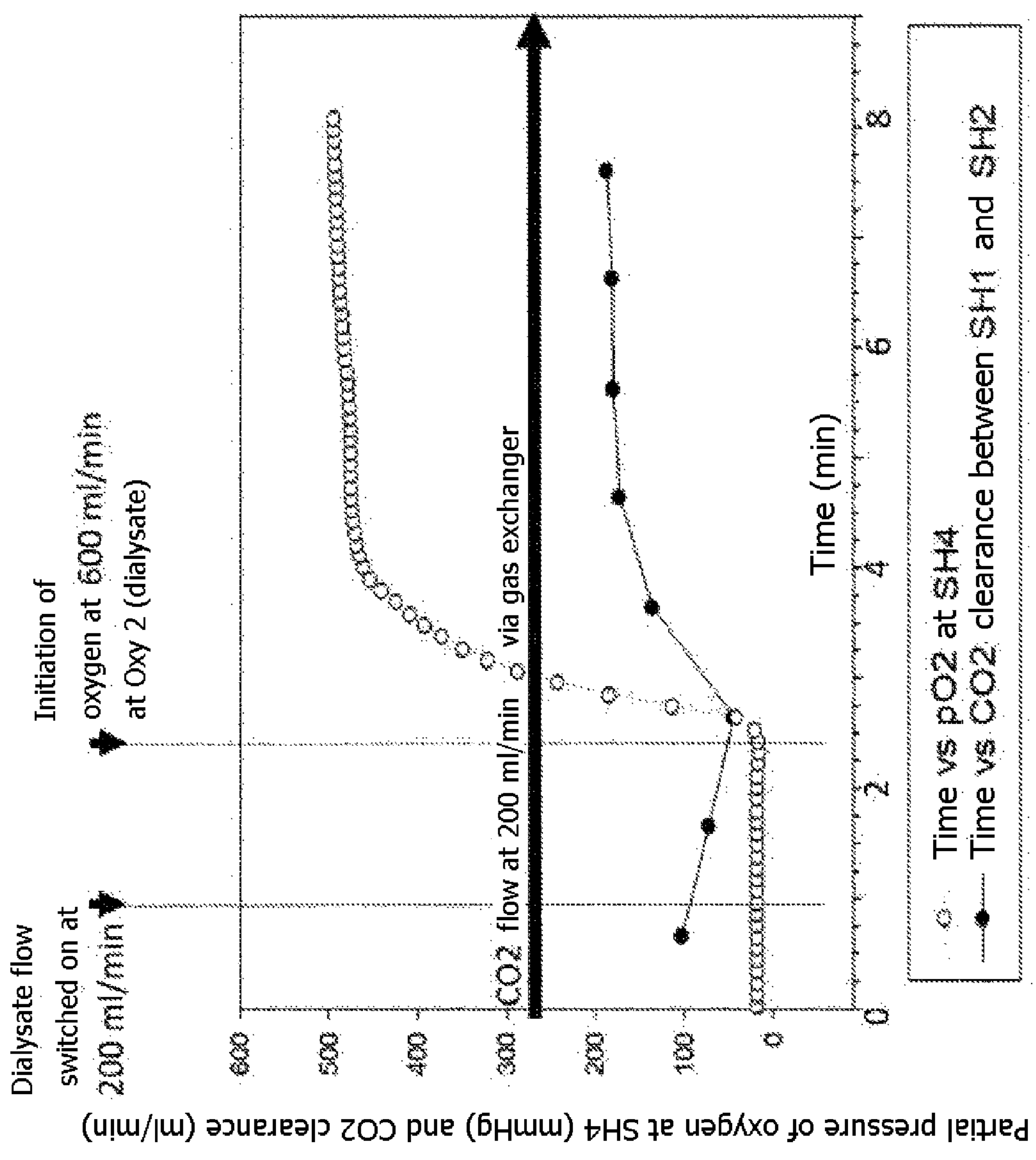
FIG. 2 shows a graphical representation of CO2 clearance.

FIG. 2 shows $CO_2$ clearance via the dialyzer (black points), calculated via the drop in $CO_2$ concentration over the dialyzer between the sensors SH1 and SH2 in FIG. 2 and the blood flow (200 ml/min), plotted with the partial pressure of oxygen of the incoming dialysate. It is clear that it is not the dialysis (200 ml/min) with hemoglobin itself which increases $CO_2$ clearance ($CO_2$ input of 200 ml/min at the gas exchanger (GE)); instead, it is only with the input of oxygen into the hemoglobin-containing dialysate in the oxygenator 2 that the $CO_2$ clearance at the dialyzer rises rapidly and reaches practically almost 100% of the blood flow.

Figure 3:
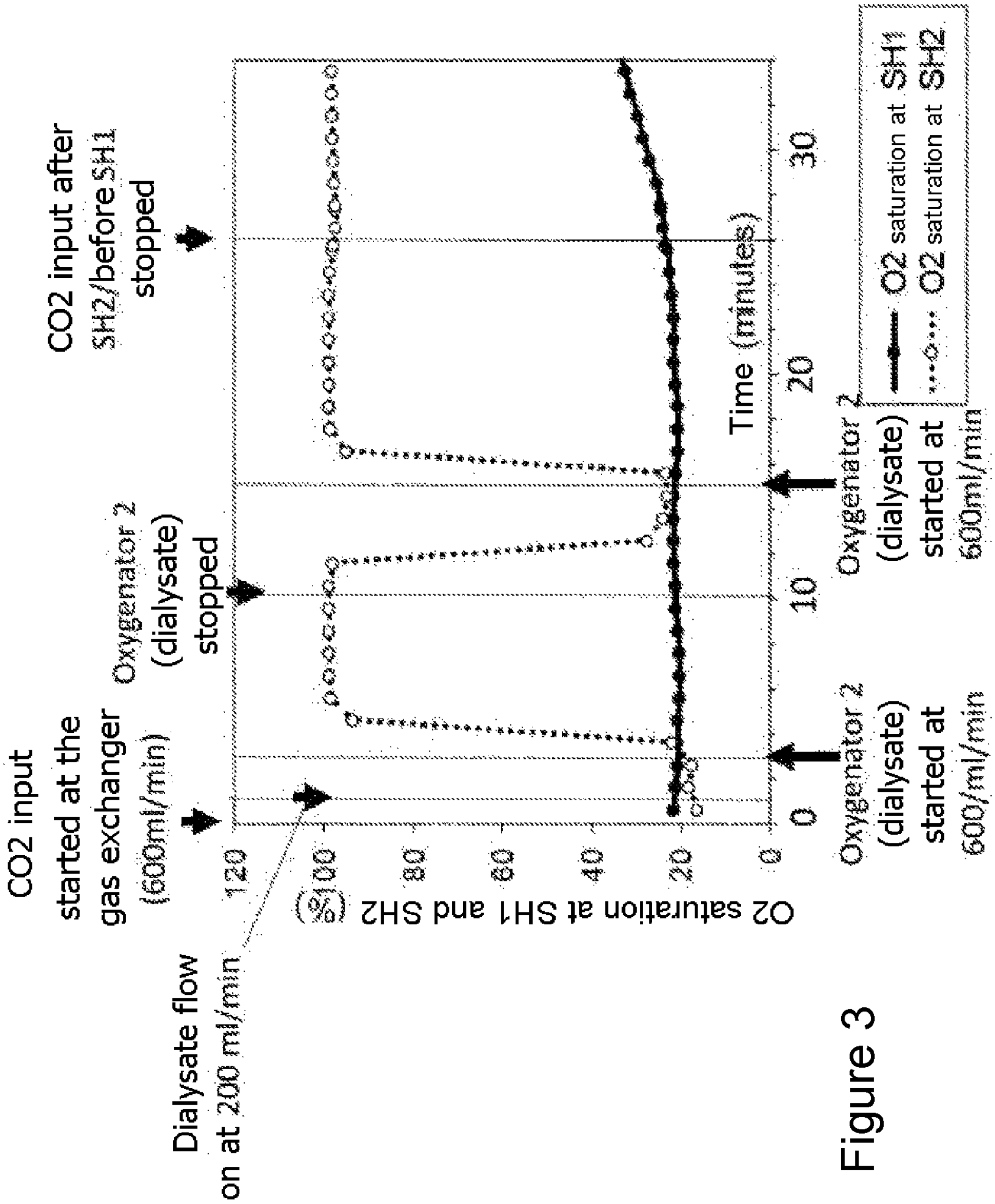
FIG. 3 shows a graphical representation of oxygen saturation of the blood.

FIG. 3 shows the oxygen saturation downstream of the dialyzer SH2 in the embodiment according to FIG. 1. The first 8 minutes correspond to the first 8 minutes of FIG. 2. Here too, it is clear that solely the circulation with hemoglobin does not have a substantial effect on oxygen saturation and that the oxygenation (1 1 $O_2$ via oxygenator 2) of the hemoglobin-containing dialysate, which starts after 4 min, is however associated with a very rapid saturation of the blood with oxygen. To illustrate the effect, the oxygen stream and the dialysate is stopped again, which results in an immediate drop at the SH2 sampling point to the SH1 values, which are greatly reduced by the input of 200 ml/min $CO_2$ at the gas exchanger GE in the blood (<20%). The oxygen is reinitiated after 15 min at (600 ml/min) and the dialysate is switched back on to 200 ml/min, which leads to rapid improvement in the $O_2$ saturation at SH2, despite 200 ml $CO_2$/min "poisoning" via the gas exchanger GE in the blood. After 20 min, this "poisoning" is switched off and the pool 3 for the composition or the solution, for example for blood, as a whole also steadily improves with oxygen saturation.

Example 2: Control

Figure 4:
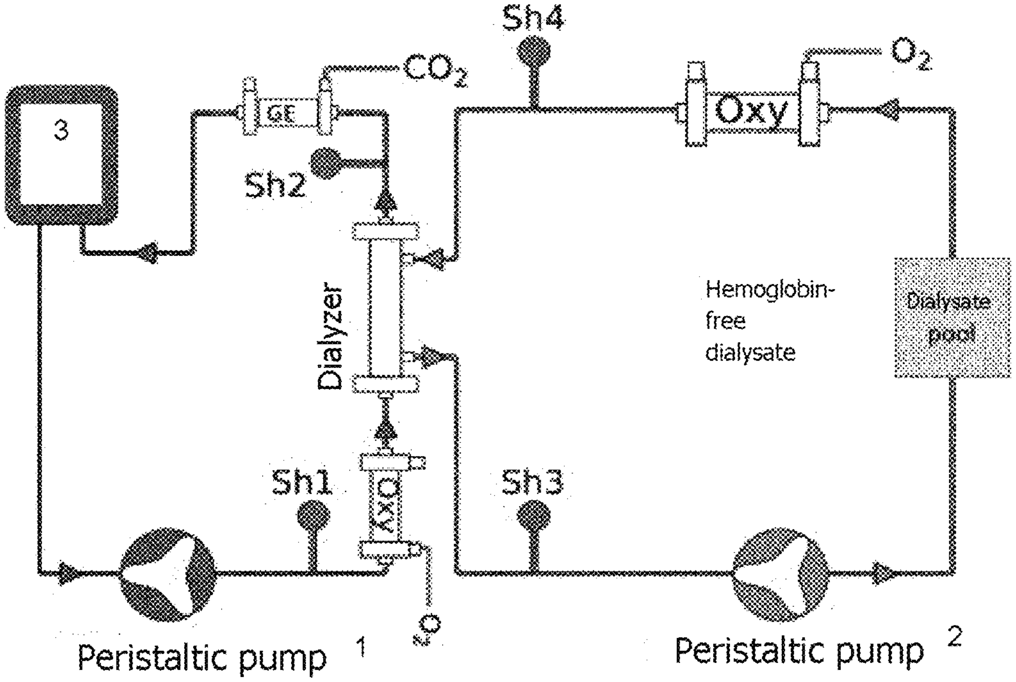
FIG. 4 shows a control experiment.

FIG. 4 shows a blood circuit (hematocrit approx. 40%) that is driven by a peristaltic pump 1 and flows through a dialyzer on the inside of the hollow fibers. As in FIG. 1, the dialyzer is a commercially available asymmetric polysulfone high-flux dialyzer (sieving coefficient for albumin <10%, or <1%), though alternative materials can also be used, such as polyamide, polyethersulfone, et cetera. The membrane is a hollow-fiber membrane or a flat membrane. Upstream and downstream of the dialyzer, the blood gases are measured at the sampling points SH1 and SH2. In order to simulate endogenous $CO_2$ poisoning, $CO_2$ is "blown in" downstream of the sensor SH2 immediately upstream of the pool 3 for blood via a gas exchanger (for example, oxygenator).

After the sensor SH1 in the direction of flow, classic oxygenation and $CO_2$ elimination is performed by an hemo-oxygenator ($O_2$ blown in and exchanged for $CO_2$, similar to a simple oxygenator). The combined effect of oxygenator and dialysis is measured downstream of the dialyzer at SH2. In such embodiments, the dialysate is commercially available dialysate that is likewise driven by a pump 2, for example a peristaltic pump. On the dialysate side as well, blood gas analysis is performed upstream SH4 and downstream SH3 of the dialyzer.

The dialysate can be operated in cocurrent or countercurrent, preference being given to countercurrent. The effect of this classic hemo-oxygenation on the $CO_2$ clearance via the entire system is demonstrated in FIG. 5. The effect on the oxygen saturation of the blood is shown in FIG. 6.

The significance of the oxygen/$SO_2$ carrier in the blood is additionally demonstrated by, as an additional control experiment, sequential connection of the option of oxygenation of the hemoglobin-free dialysate from a dialysate pool, and this is why an identical synergy oxygenator is also installed in the dialysate. This comes into operation only in the second part of the experiment.

Figure 5:
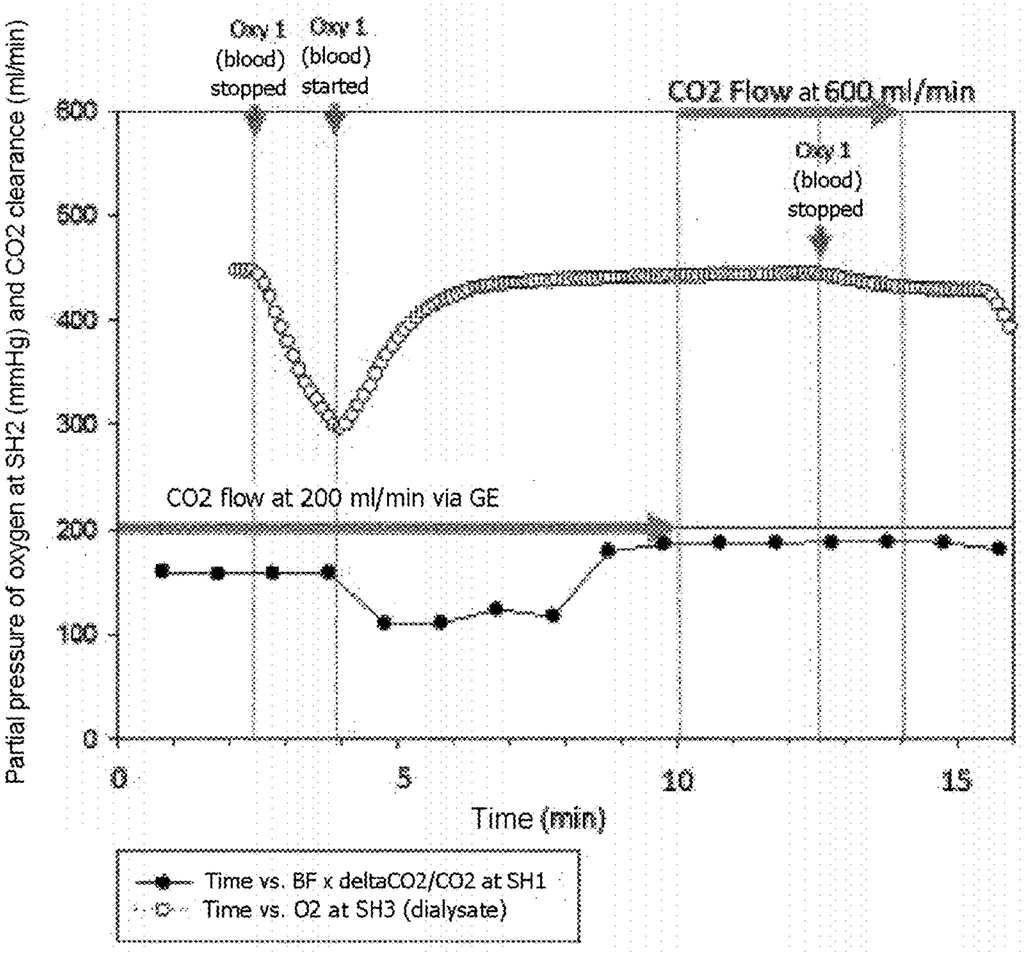
FIG. 5 shows a graphical representation of classic Nemo-oxygenation on CO2 clearance via the entire system; and, FIG. 6 shows a graphical representation of oxygen saturation of the blood.

FIG. 5 shows the $CO_2$ clearance via the oxygenator and dialyzer (black points), calculated via the drop in $CO_2$ concentration over the oxygenator and dialyzer between the sensors SH1 and SH2 in FIG. 4 and the blood flow (200 ml/min), plotted with the partial pressure of oxygen at the exiting dialysate SH3—corresponds to the partial pressure of O2 prevailing in the system. The combined oxygenation and dialysis at 200 ml achieves good oxygenation, the synergy dialyzer being a highly effective dialyzer that is actually customary for full oxygenation at approx. 5 l/min.

Figure 6:
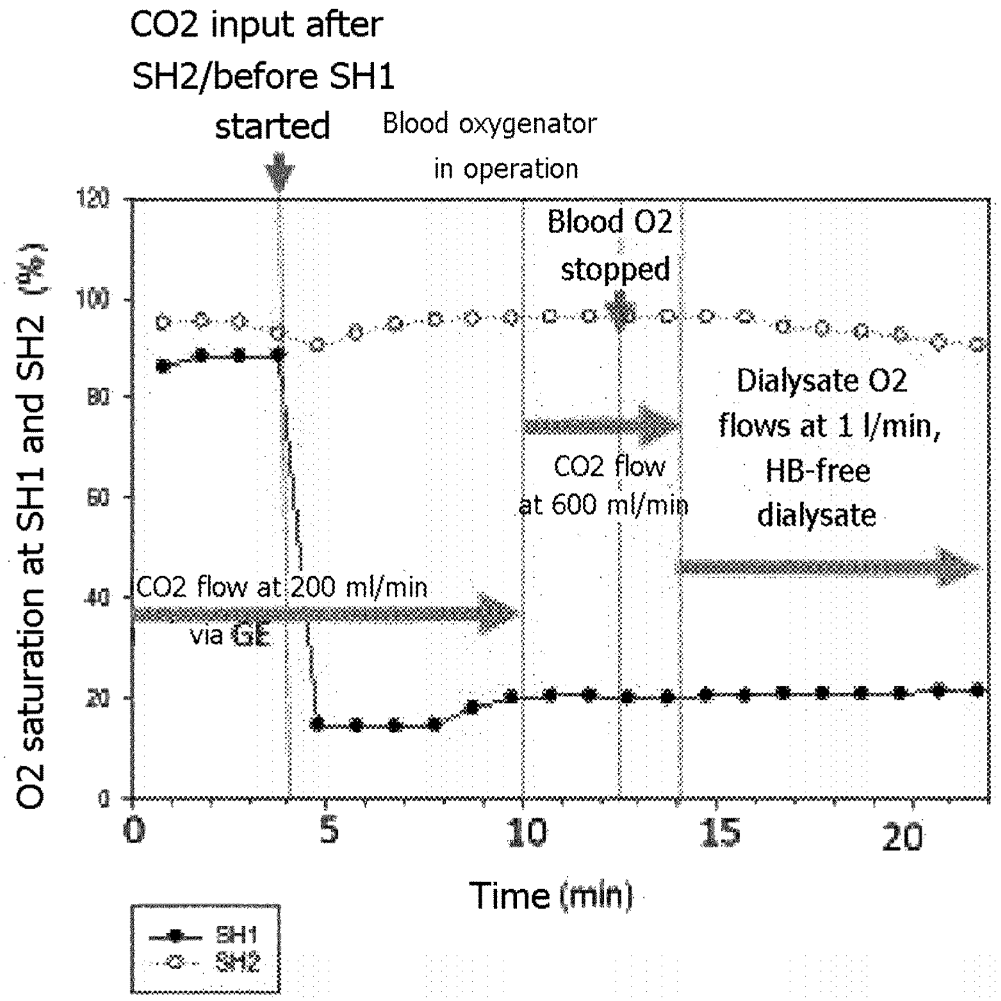

FIG. 6 shows the oxygen saturation downstream of the dialyzer SH2 in the control experiment according to FIG. 4. In the case of full oxygenation with 1 liter O2 via the oxygenator (synergy) beginning after 4 minutes, full oxygenation is achieved in line with the prior art. After the CO2 "poisoning flow" and the oxygenation in the blood oxygenator are stopped, the oxygen saturation starts to fall slowly; even the oxygenation of the hemoglobin-free dialysate switched on at the end is not able to rapidly raise the oxygen saturation in SH2 as in FIG. 3.

Exemplary Further Embodiments

A further embodiment is a method for influencing the concentration of gases such as oxygen (O2) and/or carbon dioxide (CO2) in a composition or a solution of biological or complex chemical fluids, in which the composition or the solution is guided one-sidedly along an asymmetric, semi-permeable membrane, and a dialysate is guided on the other side of the same membrane, which dialysate is oxygenated in a closed circuit containing an oxygenator, characterized in that the composition or solution to be influenced contains corpuscular gas carriers (erythrocytes) and the dialysate in the closed circuit contains a gas carrier for at least one of the gases to be influenced, via which the gas to be influenced is taken as closely as possible to the composition or the solution, wherein the gas carrier gets close to the composition or the solution owing to an asymmetric pore structure of the membrane with more-open pores on the dialysate side, such that oxygen (O2) diffuses into the composition or the solution over a shortest possible distance and, at the same time, carbon dioxide (CO2) is withdrawn from the composition or the solution into the dialysate by diffusion over a shortest possible distance without the gas carrier itself passing through the membrane, wherein, for regeneration, the dialysate is regenerated by fresh new input of oxygen (O2) and/or by withdrawal of carbon dioxide (CO2).

A further embodiment of the above method is characterized in that the gas carrier used is molecular hemoglobin or other related proteins.

According to a further embodiment of the above methods, the gas carrier gets close to the composition or the solution owing to an asymmetric pore structure of the membrane with more-open pores on the dialysate side of up to below 50 μm, preferably below 1 μm and most preferably below 100 nm, wherein the gas carrier, however, passes through the membrane to an extent of not more than 10%, preferably less than 0.1% and most preferably less than 0.01%, such that oxygen (O2) diffuses into the composition or the solution over a shortest possible distance and, at the same time, carbon dioxide (CO2) is withdrawn from the composition or the solution into the dialysate by diffusion over a shortest possible distance without the gas carrier itself passing through the membrane.

According to a further embodiment of the above methods, on the dialysate side, the concentration of the gas carrier is set higher than the concentration of the blood hemoglobin, thereby additionally increasing the mass transfer of CO2 and oxygen.

According to a further embodiment of the above methods, the loaded or unloaded gas carrier is regenerated in a closed recirculation circuit in a secondary manner via a device by loading and/or unloading of gas.

According to a further embodiment of the above methods, the regeneration of the gas carrier in the dialysate is done by the oxygenator, which regenerates the carrier-bearing dialysate by withdrawal of carbon dioxide (CO2) and/or fresh new input of oxygen (O2).

According to a further embodiment of the above methods, the membrane used is an asymmetric high-flux dialysis membrane having a cut-off between 120 and 1 KD, preferably between 60 and 10 KD and particularly preferably 20 and 50 KD.

According to a further embodiment of the above methods, the dialysate contains molecular hemoglobin having a molecular weight of less than 1 megadalton (approx. 20 hemoglobin tetramers, cross-linked), preferably of less than 500 kD (approx. 10 hemoglobin tetramers, cross-linked) and most preferably below 60 kD (one tetramer).

According to a further embodiment of the above methods, the dialysate is used for extracorporeal treatment of blood, containing electrolytes, buffer, sugar, molecular monomeric or multimeric hemoglobin and/or albumin as components, wherein the electrolytes, buffer and glucose vary within the concentrations of commercially available concentrates, wherein the molecular hemoglobin is concentrated in the concentration between greater than 0 g/l up to the technical solubility limit, preferably above 30 g/l and particularly preferably above 70 g/l, and albumin is concentrated with a concentration between greater than 0 g/l up to the technical solubility limit, preferably above 50 g/l and particularly preferably above 200 g/l.

According to a further embodiment of the above methods, the dialysate contains carbonic anhydrase present as a monomer or functionally cross-linked as a dimer or multimer in order to allow passage into the open-pore dialysate side of the membrane, and to prevent passage into the composition or solution to be influenced on the narrow-pore side of the membrane to an extent of at least 80%, preferably 95% and ideally above 99%.

According to a further embodiment of the above methods, the membrane is simultaneously used for detoxification by dialysis or filtration in the context of blood purification methods with dialysis or apheresis methods.

A further embodiment is an arrangement for influencing the concentration of gases such as oxygen (O2) and/or carbon dioxide (CO2) in a composition or a solution of biological or complex chemical fluids, wherein the arrangement is connectable to a pool (3) and consists of two circuits, wherein a first circuit is used for supplying the composition or the solution one-sidedly along a narrow-pore side of an asymmetric, semipermeable membrane from the pool (3) via hoses and pumps, wherein the composition or the solution is then conducted back into the pool (3) via hoses, and a second circuit is used for supplying a dialysate other-sidedly along an open-pore side of the asymmetric, semipermeable membrane via hoses and pumps, wherein the dialysate contains a gas carrier in the form of molecular hemoglobin or other related proteins for the gas to be influenced, and wherein the gas carrier, owing to an asymmetric pore structure of the membrane with more-open pores on the dialysate side, can penetrate said membrane and thus get close to the composition or the solution before the decreasing pores of the asymmetric membrane prevent through-passage, the exchange of dissolved gas takes place, and the dialysate is then conducted back via hoses into a recirculation circuit over a device for regeneration by loading and/or unloading of gases, wherein the dialysate is regenerated in the device for regeneration by fresh new input of oxygen (O2) and/or by withdrawal of carbon dioxide (CO2).

A further embodiment of the above arrangement is characterized in that the pumps are roller pumps, impeller pumps or membrane pumps and the asymmetric, semipermeable membrane is a flat or hollow-fiber membrane.

According to a further embodiment of the above arrangements, the gas carrier gets close to the composition or the solution owing to an asymmetric pore structure of the membrane with more-open pores on the dialysate side of up to below 50 μm, preferably below 1 μm and most preferably below 100 nm, wherein the gas carrier, however, passes through the membrane to an extent of not more than 10%, preferably less than 0.1% and most preferably less than 0.01%, such that oxygen (O2) diffuses into the composition or the solution over a short distance and, at the same time, carbon dioxide (CO2) is withdrawn from the composition or the solution into the dialysate by diffusion over a short distance without the gas carrier itself passing through the membrane.

According to a further embodiment of the above arrangements, the device for regeneration is a commercially available oxygenator.

According to a further embodiment of the above arrangements, the composition or the solution is blood or plasma, and in that a dialyzer which allows diffusive transfer of pore-crossing molecules from the blood or plasma into a dialysate through a semipermeable membrane is comprised.

According to a further embodiment of the above arrangements, for extracorporeal treatment of blood or plasma in a closed circuit, the dialysate is regenerated both by switching on the device for regeneration and by additional adsorption and/or dialysis and/or filtration for material removal or input.

According to a further embodiment of the above arrangements, the device for regeneration contains assimilative biological systems which can convert carbon dioxide and water into glucose and oxygen on the basis of photosynthesis under the influence of light.

According to a further embodiment of the above arrangements, the device for regeneration uses electrochemical processes for oxygen production.

It is understood that the foregoing description is that of the preferred embodiments of the invention and that various changes and modifications may be made thereto without departing from the spirit and scope of the invention as defined in the appended claims.

What is claimed is:

1. A method for influencing gas concentration in a liquid composition, wherein gases comprise oxygen and/or carbon dioxide, which comprises:

introducing the liquid composition via hoses into a dialyzer on one-side of an asymmetric, semipermeable dialysis membrane, said asymmetric, semipermeable membrane having an asymmetric pore structure, comprising: (a) more-open first pores oriented on a dialysate side, and (b) narrower second pores, of a size narrower than the more-open first pores, on a liquid composition side, introducing a dialysate on the dialysate side of the asymmetric, semipermeable membrane, wherein the dialysate is oxygenated in a closed circuit system comprising an oxygenator, wherein the liquid composition comprises corpuscular gas carrier molecules, wherein the dialysate comprises molecular gas carrier molecules for at least one of the gases, said molecular gas carrier molecules being of a size sufficient to enter the more-open first pores on the dialysate side but insufficient to pass through the narrower second pores on the liquid composition side, wherein said asymmetric, semipermeable membrane provides sufficient proximity of said molecular gas carrier molecules to said liquid composition to facilitate gas exchange without allowing the molecular gas carrier molecules to cross the asymmetric, semipermeable membrane, and wherein the dialysate is regenerated by addition of the oxygen and/or removal of the carbon dioxide.

2. The method of claim 1, wherein the molecular gas carrier molecules in the dialysate comprise molecular hemoglobin.

3. The method of claim 1, wherein the more-open first pores on the dialysate side are less than 50 μm in diameter, and wherein the molecular gas carrier molecules pass through the asymmetric, semipermeable membrane to an extent of not more than 10%.

4. The method of claim 1, wherein the liquid composition is blood, and wherein, on the dialysate side, a concentration of the molecular gas carrier molecules is higher than a concentration of hemoglobin in erythrocytes that are in the liquid composition.

5. The method of claim 1, wherein the molecular gas carrier molecules in the dialysate for the at least one of the gases is regenerated in a closed recirculation circuit in a secondary manner via a device by loading and/or unloading of the at least one of the gases.

6. The method of claim 5, wherein the device is the oxygenator that regenerates a carrier-bearing dialysate by withdrawal of the carbon dioxide and/or input of the oxygen.

7. The method of claim 1, wherein the asymmetric, semipermeable membrane is an asymmetric high-flux dialysis membrane comprising a molecular weight cut-off of between 120 kDa and 1 kDa.

8. The method of claim 2, wherein the molecular hemoglobin in the dialysate has a molecular weight of less than 1 megadalton.

9. The method of claim 2, wherein the liquid composition is blood, and the dialysate comprises electrolytes, buffer, sugar, molecular monomeric hemoglobin, multimeric hemoglobin, and/or albumin.

10. The method of claim 1, wherein the dialysate comprises carbonic anhydrase present as a monomer or functionally cross-linked as a dimer or multimer.

11. The method of claim 1, wherein the corpuscular gas carrier molecules are erythrocytes.

12. An arrangement for influencing gas concentration in a liquid composition, wherein gases comprise oxygen and/or carbon dioxide, and wherein the arrangement comprises a pool, that hosts the liquid composition, and connected hoses, by which:

the liquid composition is introduced by a pump into a dialyzer on one side of an asymmetric, semipermeable dialysis membrane, said asymmetric, semipermeable membrane having an asymmetric pore structure, comprising: (a) more-open first pores oriented on a dialysate side, and (b) narrower second pores, of a size narrower than the more-open first pores, on a liquid composition side;

the pool comprises a dialysate and second connected hoses and second pump introducing the dialysate on an opposite side of the asymmetric, semipermeable membrane, wherein said dialysate is oxygenated in a closed-circuit system comprising an oxygenator within a circuit, wherein the dialysate comprises a molecular gas carrier molecule for at least one of the gases, said molecular gas carrier molecule being of a size sufficient to enter the more-open first pores on the dialysate side but insufficient to pass through the narrower second pores on the liquid composition side, wherein said asymmetric, semipermeable membrane provides sufficient proximity of said molecular gas carrier molecule to said liquid composition to facilitate gas exchange without allowing the molecular gas carrier molecule to cross the asymmetric, semipermeable membrane, and wherein the dialysate is regenerated by addition of the oxygen and/or removal of the carbon dioxide.

13. The arrangement of claim 12, wherein the pump and second pump are roller pumps, impeller pumps, or membrane pumps, and wherein the asymmetric, semipermeable membrane is a flat or hollow-fiber membrane.

14. The arrangement of claim 12, wherein the more-open first pores of the asymmetric, semipermeable membrane have a diameter of less than 50 μm on the dialysate side.

15. The arrangement of claim 13, wherein the liquid composition is blood or plasma.

16. The arrangement of claim 12, wherein the dialysate is regenerated both by switching on the oxygenator and by additional adsorption, dialysis, and/or filtration for material removal or input.

17. The arrangement of claim 12, further comprising electrochemical processes for oxygen production.

18. The method of claim 12, wherein the pump is a roller pump.

19. The method of claim 12, wherein the molecular gas carrier molecule is hemoglobin.

20. The method of claim 12, wherein the asymmetric, semipermeable membrane is comprised of polysulfone or polyethersulfone.

* * * * *